(12) United States Patent
Gall

(10) Patent No.: US 6,806,268 B2
(45) Date of Patent: Oct. 19, 2004

(54) METHOD FOR TREATING GLAUCOMA V

(75) Inventor: Martin Gall, Morristown, NJ (US)

(73) Assignee: Alteon, Inc., Parsippany, NJ (US)

( * ) Notice: Subject to any disclaimer, the term of this patent is extended or adjusted under 35 U.S.C. 154(b) by 16 days.

(21) Appl. No.: 10/158,683

(22) Filed: May 30, 2002

(65) Prior Publication Data

US 2002/0193376 A1 Dec. 19, 2002

Related U.S. Application Data

(60) Provisional application No. 60/294,339, filed on May 30, 2001.

(51) Int. Cl.[7] ............ C07D 487/04; A61K 31/53; A61K 31/519; A61K 31/437; A61P 27/02

(52) U.S. Cl. ............ 514/228.5; 544/61; 544/113; 544/194; 544/211; 544/263; 544/281; 514/233.2; 514/246; 546/119; 546/121

(58) Field of Search ............ 544/61, 113, 194, 544/211, 212; 514/233.2, 246, 228.5

Primary Examiner—Mark L. Berch
Assistant Examiner—Kahsay Habte
(74) Attorney, Agent, or Firm—Mintz, Levin, Cohn, Ferris, Glovsky and Popeo, P.C.; Ivor R. Elrifi

(57) ABSTRACT

Provided, among things, is a method of decreasing intraocular pressure in an animal, including a human, comprising administering an intraocular pressure decreasing amount of a compound of the formula IA and or IB:

IA

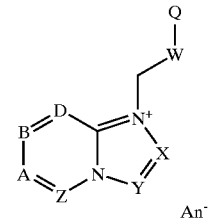

IB

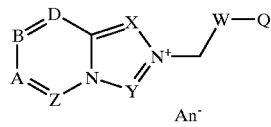

7 Claims, No Drawings

METHOD FOR TREATING GLAUCOMA V

This application claims the priority of U.S. Application Ser. No. 60/294,339, filed May 30, 2001.

The present invention relates to methods for treating glaucoma or improving accommodation (i.e. the process by which the eye adjusts for vision at different distances).

In one aspect, the present invention relates to a method of decreasing the intraocular pressure caused by glaucoma.

Diabetes is the major determinant to the development of visual disability and blindness in parts of the world unencumbered by causes related to malnutrition or infectious diseases. Retinopathy is the leading cause of blindness in diabetics and is a progressive, degenerative disease. Of the many risk factors believed to be associated with diabetic retinopathy, the level of glucose in the plasma has been widely investigated. It is well accepted that a lower incidence of retinopathy is associated with decreased plasma levels of glucose.

Ophthalmologic disorders in diabetes include opacification and glaucoma. The occurrence of these indications is correlated with the persistent hyperglycemia of the disease. Although the incidence of glaucoma is significant in diabetic populations, glaucoma affects a substantial portion of the general aging population as well.

Primary open angle glaucoma occurs in approximately 4% of diabetics compared to 1.8% of the general population. The reasons for the increase in intraocular pressure that is observed in this disorder are not completely understood. The increase in intraocular pressure that characterizes glaucoma is likely caused by impairment in the drainage of fluid from the eye at the trabecular meshwork since trabeculectomy restores, at least for a period of time, normal intraocular pressures. The origin of this impairment to fluid movement is currently unknown but may be related to a physical obstruction or restriction to movement of proteins that make up a sieving system in the trabecular meshwork. The trabecular meshwork functions as a sieving system that maintains a restricted flow of intraocular fluid from the eye. The result of excess restriction of this flow is increased intraocular pressure.

Replacement of the trabecular meshwork (trabeculectomy) remains an established surgical procedure for improving the filtering of intraocular fluid and for overall reduction of intraocular pressure. This remedy is invasive and of limited effectiveness, since pressure elevation frequently recurs after the procedures.

Current chronic pharmaceutical therapies impose a measure of risk on an already medically compromised patient population. The use of topical B-blockers may affect underlying cardiovascular disease, and carbonic anhydrase inhibitors (e.g. Diamox™) may cause metabolic acidosis. The use of pressure-lowering drugs will be affected by the state of renal disease in compromised elderly and diabetic patients. The drawbacks associated with current pharmaceutical therapies highlight an unmet medical need for a chronic pharmaceutical intervention that is distinct in mechanism of action from current therapies.

New strategies for pharmaceutical intervention in the treatment of glaucoma based upon new mechanisms of action need to be identified. In addition, pharmaceutical agents that decrease the intraocular pressure associated with glaucoma are needed. Also, the methods of improving accommodation provided by the invention allow one to avoid costly and burdensome optical solutions, such as the use of separate reading glasses or glasses with bifocal lenses.

SUMMARY OF THE INVENTION

In one embodiment, the invention relates to a method of treating or ameliorating or preventing glaucoma, decreasing intraocular pressure or improving or ameliorating ocular accommodation in an animal, including a human, comprising administering an intraocular pressure decreasing or accommodation improving amount of a compound of the formula IA or IB:

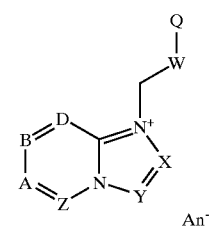

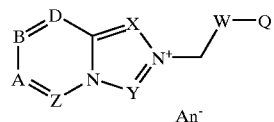

wherein:
Q is Ar* or NR'R" or together, W—Q are CN, Ar or C≡C—$R^Q$, A, B, D and Z are selected from the group N and $CR^A$, $CR^B$, $CR^D$ and $CR^Z$, respectively, and X and Y are selected from the group N, $CR^X$ and $CR^Y$, respectively, with the proviso that, including the bridgehead N, only one to three of the atoms comprising the six-membered ring of the heteroaromatic ring system, may be N; $R^A$, $R^B$, $R^D$, $R^Q$, $R^Z$, $R^X$ and $R^Y$, the anions An⁻, and W, Ar and Ar* are defined further below.

DETAILED DESCRIPTION OF THE INVENTION

In accordance with the present invention a method is provided for the treatment of an animal, preferably a mammal, preferably a human with ophthalmologic disorders including glaucoma and reduced accommodation. Briefly the method of the present invention provides for a method of treatment of mammals with glaucoma or reduced accommodation that can be caused by age or certain age-related diseased states such as diabetes. The method provides for administration of classes of inhibitors of advanced glycation or breakers of advanced glycosylated end-products. The invention further provides for methods to monitor the improvement in the ocular condition during the course of the administration of compound.

Primary open angle glaucoma is characterized by an increase in intraocular pressure. The condition of open angle glaucoma is characterized by an increase in the pressure within a person's eye or eyes, called the intraocular pressure. The normal pressure is about 15 mm Hg. Elevated pressures of 20–30 mm Hg create a strong risk of damage to the optic nerve and blindness.

Glucose reacts with proteins by a non-enzymatic, post-translational modification process called non-enzymatic glycosylation. The resulting sugar-derived adduct, the advanced glycosylation end product (AGE), matures to a molecular species that is reactive, and can readily bond to amino groups on adjacent proteins, resulting in the formation of AGE crosslinks between proteins.

It has now been found that certain compounds that inhibit the formation of such sugar-derived adducts, or in some cases are believed to deactivate such adducts or break resulting crosslinks, can reduce intraocular pressure or ameliorate a trend towards elevated pressure.

Structural matrix proteins isolated from tissues of diabetics and aged individuals are more highly cross-linked than those from nondiabetics or younger individuals and are more resistant to both enzymatic and chemical hydrolysis in vitro. It is this cross-linked state of proteins that is believed to cause stiffness of tissues. The cleavage of AGE cross-links between proteins can provide a mechanism-based therapy for restoration of normal tissue function. An agent that cleaves AGE crosslinks between proteins or inhibits their formation can restore more normal sieving function and movement to the trabecular meshwork.

In accordance with the present invention, methods for administering pharmaceutical compositions containing certain compounds have been developed for reducing the intraocular pressure associated with glaucoma. These agents are derived from fused, 6-, 5-membered bicyclic heteroaromatic rings containing nitrogen as one of the two bridging atoms as shown in the Summary section above. For example, the compounds can be derived as shown in Scheme 1 below.

Scheme 1

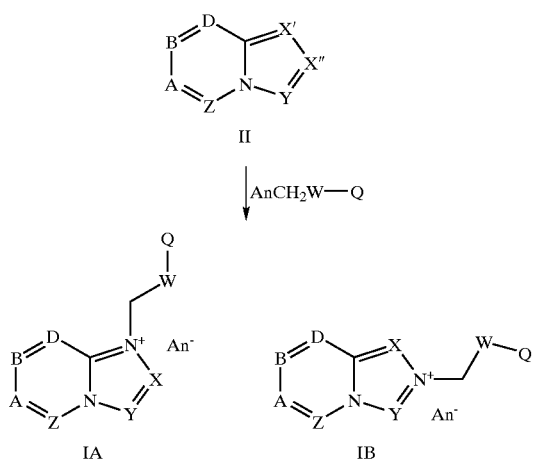

| | |
|---|---|
| $IA_1$ or $IB_1$ | for W = CO, Q = Ar* |
| $IA_2$ or $IB_2$ | for W = CO, Q = NR'R" |
| $IA_3$ or $IB_3$ | for W—Q =Ar |
| $IA_4$ or $IB_4$ | for W—Q =C≡C—$R^Q$ |
| $IA_5$ or $IB_5$ | for W—Q =CN |

"An" can be any suitable leaving group such as chloride, bromide, mesylate, tosylate, brosylate, or mesitylene-sulfonate.

It is recognized by those skilled in the art that when each X'=N (Scheme 1), alkylation with $AnCH_2WQ$ may occur on either nitrogen to yield mixtures of IA (X=N) and IB (X=N), with IB being the predominant isomeric product. For those cases in which Z, B, D or particularly A, is N, alkylation at that position of the 6-membered ring bicyclic heteroaromatic moiety might be expected to compete with the desired reaction on the 5-membered ring heteroaromatic moiety. In this situation, the addition of one equivalent or less of a suitable acid, such as the appropriate volume of an ethereal HCl or ethereal HBr solution prior to the addition of $AnCH_2WQ$, would be expected to alter the ratio of the isomers formed. Where isomeric addition products are formed, they may be separated by chromatographic methods such as HPLC or, more preferably, by selective crystallization.

The preferred compounds of the present invention are derived from [1,2a]-imidazopyridines, [1,2a]-imidazopyrimidines, [1,2a]-imidazo[1,3,5]-triazines, [3,4a][1,2,4]-triazolo-pyridines, [3,4a][1,2,4]-triazolopyrimidines, [3,4a][1,2,4]-triazolo[1,3,5]-triazines, [3,4a]-imidazopyridines, [3,4a]-imidazopyrimidines, [3,4a][1,2,3]-triazolopyridines, [3,4a][1,2,3]-triazolopyrimidines, [1,5a]-tetrazolopyridines, [1,5a]-tetrazolopyrimidines, and the like, by their treatment with $AnCH_2CQ$, neat, or in a suitable polar solvent, such as acetonitrile, dimethylformamide, N-methyl-pyrrolidone, dimethylsulfoxide, methanol, ethanol or trifluoromethanol, or aqueous mixtures of these organic solvents, at from room temperature to 60° C. for from 1 to 48 hours. (See Scheme 1.)

It will also be recognized by those skilled in the art that asymmetric carbons in the compounds of the invention can exist in one of two configurations, (R) or (S). When equal mixtures of (R) and (S) forms are present, the compound exists as a non-optically active racemic mixture. The present invention covers the racemates and each single, optically pure or enriched enantiomeric derivative. It will further be recognized that the tools for isolating enantiomers with chiral specific chromatographic methods and crystallographic methods (typically using chiral salts) have developed to make such isolations generally applicable.

The alkyl and alkenyl groups referred to below include both $C_1$ to $C_6$ linear and branched alkyl and alkenyl groups, unless otherwise noted. In addition, alkoxy groups include linear or branched $C_1$ to $C_6$ alkoxy groups, unless otherwise noted. Alkyl' represents a second alkyl group independently selected from the same $C_1$ to $C_6$ linear or branched selection.

A, B, D and Z are independently N or, respectively, $CR^A$, $CR^B$, $CR^D$ or $CR^Z$, with the proviso that, including the bridgehead N atom, only one to three of the atoms comprising the six-membered ring of the heteroaromatic ring system may be N.

$R^A$, $R^B$, $R^D$ and $R^Z$ are independently hydrogen, alkyl, alkoxy, allyl, alkylalkynyl, amino, acylamino, aroylamino, (aryl)(alkyl)amino, diarylamino, dialkylamino, pyrrolidin-1-yl, piperidin-1-yl, 4-arylpiperidin-1-yl, 4-arylpiperazin-1-yl, 1-morpholin-4-yl, 1-thiamorpholin-4-yl, alkylthio, alkoxycarbonyl, carboxy, $(C_1–C_6)$-hydroxyalkyl, $H_2NS(O)_2$, $H_2NC(O)$, (alkyl)(alkyl')NC(O), 4-arylpiperazin-1-yl-C(O), fluoromethyl, difluoromethyl, trifluoromethyl, alkyl sulfonyl, alkylsulfinyl or arylsulfonyl.

X and Y are independently N, N+(O—), or, respectively, $CR^X$ or $CR^Y$, with the proviso that there is only zero to one N-oxide.

$R^X$ and $R^Y$ are independently acetamido, hydrogen, alkyl, amino, —C≡$CR^E$, —$CH_2$—C≡$CR^E$, alkylamino, dialkylamino, alkylthio, aryl, arylthio, arylalkyl, hydroxyalkyl, fluoromethyl, difluoromethyl, trifluoromethyl, cyanomethyl, alkoxycarbonylmethyl, 1-(alkoxycarbonyl)-1-hydroxyalkyl or aminocarbonylmethyl, wherein $R^E$ is alkyl, hydrogen or hydroxyalkyl. The "1" notations of "1-(alkoxycarbonyl)-1-hydroxyalkyl" indicates that a terminal methyl [but for the recited substitutions] of "alkyl" is substituted with the hydroxyl and esterified carbonyl [e.g., 1-(methoxycarbonyl)-1-ethanol].

W is C=O, CH(OH), $S(O)_2$ or S(O), or together with Q forms W—Q. Q is Ar* or NR'R", or, W—Q together are Ar, cyano or —C≡$CR^Q$. $R^Q$ is hydrogen, acylaminoalkyl, aroylaminoalkyl, alkyl, hydroxyalkyl, alkylaminoalkyl, dialkylaminoalkyl, (aryl)(alkyl)aminoalkyl, fluoromethyl, difluoromethyl, trifluoromethyl, Ar, ArCO, $ArS(O)_n$, where n=1 or 2, $H_2NC(O)$, or 4-arylpiperazin-1-yl-C(O).

R' and R" are independently hydrogen, alkyl, Ar, or together, NR'R" form a pyrrolidin-1-yl, piperidin-1-yl, 4-arylpiperidin-1-yl, 4-arylpiperazin-1-yl, 4-alkyl-piperazin-1-yl, 1-morpholin-4-yl or 1-thiamorpholin-4-yl ring.

An– is a pharmaceutically acceptable anion.

Ar*, Ar or aryl (consistent with the rules of aromaticity) each refer to a $C_6$ or $C_{10}$ aromatic ring, or a 5- or 6-membered heteroaromatic ring containing at least one and up to three atoms of N for the 6-membered heteroaryl ring and from one to three atoms of N or one atom of O or S and zero to two atoms of N for the 5-membered heteroaryl ring; each heteroaryl ring may be optionally substituted with up to two amino-, dialkylamino-, pyrrolidin-1-yl, piperidin-1-yl, 1-morpholin-4-yl, 1-thiamorpholin-4-yl, 4-arylpiperidin-1-yl, 4-arylpiperazin-1-yl-, or halo groups, or fused to a substituted benzene, pyridine, pyrimidine, pyridazine or triazine ring, and wherein $C_6$ or $C_{10}$ aromatic and heteroaromatic rings can be additionally substituted as set forth below.

$C_6$ or $C_{10}$ aromatic rings (including Ar, Ar*, or aryl), can be additionally substituted with acylamino, acyloxyalkyl, alkanoyl, alkanoylalkyl, alkenyl, alkoxy, alkoxycarbonyl, alkoxycarbonylalkyl, alkyl, —C≡$CR^E$, alkylamino, ($C_1$–$C_3$)-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, (C1–C6)-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl.

Heteroaromatic rings (Ar, Ar*, or aryl), can be additionally substituted with groups selected from: acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, 1-morpholin-4-yl, 1-thiamorpholin-4-yl, 4-arylpiperazin-1-yl, sulfamoyl, aminosulfonyl ($H_2NSO_2$—), fluoromethyl, difluoromethyl or trifluoromethyl.

The halo atoms can be fluoro, chloro, bromo or iodo.

The compounds of formula IA and IB comprise biologically and pharmaceutically acceptable salts. Useful salt forms include the halides, particularly bromide and chloride, brosylate, tosylate, methanesulfonate (mesylate), and mesitylenesulfonate salts. It is recognized that appropriate acetate, fumarate, maleate and succinate derivatives may be prepared from the chloride salt via ion exchange techniques. Other related salts can be formed using similarly non-toxic, and biologically and pharmaceutically acceptable anions.

Compounds of the formula II can be conveniently prepared by chemical syntheses well-known in the art. Certain of the compounds are known and readily prepared by synthetic methods specifically published therefore.

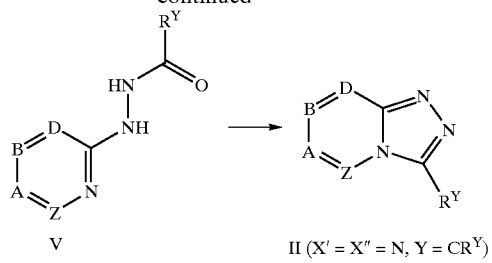

[3,4a][1,2,4]-triazolo-fused pyridines, pyrimidines or triazines [II (X'=X"=N, Y=$CR^Y$)] are prepared from the corresponding halo, particularly fluoro, substituted heterocycles (III) (many available commercially) by treating them with an appropriate alkanoyl- or aroyl-hydrazide (IV) in a solvent such as n-butanol at temperatures from 25 C. to 40° C. to isolate the amidrazone intermediate (V) or at 40° C. to preferably reflux temperature to form the fused bicyclic ring system, II. (See Scheme 2.) Corresponding 2-thiono-pyridines or pyrimidines may also be used as starting materials, in place of III.

[1,2a]-imidazopyridines, pyrimidines and triazines may be prepared by treating the halo or methoxy intermediate III with an aminoacetal, such as VI, in a solvent such as n-butanol or dimethylformamide to afford the substituted amidine, VII, which is cyclized in concentrated sulfuric acid or $TiCl_4$ in an ethereal solvent, such as 1,2-dimethoxyethane, at from 0° C. to room temperature to afford II (X'=CH, X"=N, and Y=$CR^Y$). (See Scheme 3.)

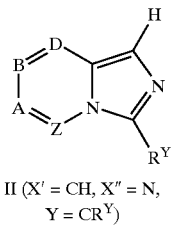

II (X' = CH, X" = N, Y = CR$^Y$)

The isomeric [1,5a]-imidazo-pyridine, pyrimidine and triazines are prepared from the appropriate cyano derivatives, VIII, (or nitromethane analogs) by reduction followed by cyclization with an orthoester, such as a triethylorthoester, to afford II (X'=CH, X"=N, and Y=CR$^Y$ (see Scheme 4), wherein R$^Y$ is hydrogen, alkyl or aryl, optionally substituted as described above.

Scheme 5

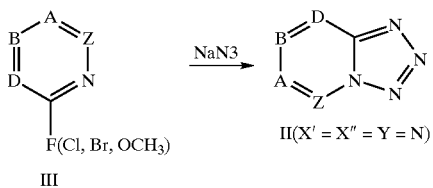

III      II(X' = X" = Y = N)

The tetrazole fused pyridines, pyrimidines and triazines [II (X'=X"=Y=N)] are prepared by treating substrate III with sodium azide in dimethyformamide or dimethylsulfoxide at 25° C. to 80° C. for 1–24 hours, as illustrated in Scheme 6.

Pharmaceutical compositions of the invention include administering an intraocular pressure decreasing amount of a compound of the formula IA or IB.

To treat glaucoma or reduced accommodation, and their associated symptoms, an "effective amount" of a pharmaceutical compound will be recognized by clinicians. The amount of the compound administered includes an amount effective to reduce, ameliorate or eliminate one or more symptoms of the disease to be treated or the condition to be avoided or treated, or to otherwise produce a clinically recognizable change in the pathology of the disease or condition.

In treating glaucoma, agents of the inventions can be administered concurrently or in a combined formulation with one or more $\alpha_2$-selective adrenergic agonists, carbonic anhydrase inhibitors or prostaglandin analogs. Examples of $\alpha_2$-selective adrenergic agonists include clonidine, apraclonidine, guanfacine, guanabenz and methyldopa, which are administered in effective amounts as is known in the art. Examples of carbonic anhydrase inhibitors include acetazolamide, dichlorphenamide and methazolamide, which are administered in effective amounts as is known in the art. Examples of prostaglandin analogs include PGE$_2$ and PGF$_{2\alpha}$ analogs, which are administered in effective amounts as is known in the art, including effective amounts administered by topical application to the eye. Thus, the invention further provides pharmaceutical compositions comprising an agent of the invention in combination with an effective amount of an $\alpha_2$-selective adrenergic agonist, carbonic anhydrase inhibitor, prostaglandin analog, or combination thereof.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, 3$^{rd}$ Edition, 1999. Such compositions can be prepared in a variety of forms, depending on the method of administration.

In addition to the subject compound, the compositions of this invention can contain a pharmaceutically acceptable carrier. The term "pharmaceutically acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically acceptable carriers should, of course, be of sufficiently high purity and sufficiently low toxicity to render them suitable for administration to the animal being treated.

Examples of substances which can serve as pharmaceutically acceptable carriers or components thereof include: sugars, such as lactose, glucose and sucrose; starches, such as corn starch and-potato starch; cellulose and its derivatives, such as sodium carboxymethyl cellulose, ethyl cellulose, and methylcellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically acceptable carrier to be used in conjunction with the subject compound is basically determined by the way the compound is to be administered. If the subject compound is to be injected, the preferred pharmaceutically acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 or 560 mg/70 kg, more preferably from about 0.5 or 10 mg to about 210 mg/70 kg. The pharmaceutically acceptable carriers suitable to prepare unit dosage forms for peroral administration are well known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methylcellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol, and binders such as acacia, microcrystalline cellulose, carboxymethylcellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0% w/v of the compound. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcysteine, sodium metabisulfite and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, including cosolvents as needed to solvate or suspend the active agent; stabilizers or preservatives such as ascorbic acid, sodium metabisulfite, cetylpyridinium chloride or benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include one or more of preservatives or stabilizers, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention are administered through, ocular, oral, or parenteral routes, including, for example, using formulations suitable as eye drops. For ocular administration, ointments or droppable liquids may be delivered by ocular delivery systems known to the art such as applicators or eyedroppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. For information on pharmaceutical compounding, see, Remington's Pharmaceutical Sciences, 16th Ed., Mack Publishing, Easton, Pa., 1980, as well as later editions.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

Compounds of the invention can be used in conjunction with monitoring the improvement (decrease) in the intraocular pressure in a mammal using standard methodology.

The methods of the inventions can be assessed in animal models for ophthalmologic function. For example, improvements in fluid outflow facility can be studied in Rhesus monkeys treated with the compounds and methods of the invention. Aged Rhesus monkeys receive a single transcorneal injection of a test compound (of the invention) at a concentration of about 1 mM in the anterior chamber of one eye, and Barany's solution, as a control, in the adjacent eye. Needle outflow facility is measured under baseline and pilocarpine-stimulated conditions at appropriate time points (for example, 3, 8, 12 and 24 weeks) after the administration of the test compound. Increases in outflow facility in the drug treated vs. the control eye under baseline and cholinergic-stimulated (e.g. pilocarpine) conditions at the various time points are compared. Various routes of administering the cholinergic agent can be studied to determine their influence on outflow facility measured in the experiments. For instance, an intravenous administration versus a direct administration of pilocarpine can be compared. The above experiment demonstrates one method of measuring the improvement in ophthalmologic function.

In addition to measuring increased fluid outflow facility using the methods of the invention, improvements in pilocarpine-stimulated accommodation (i.e, the process of effecting refractive changes in the shape of the lens) can also be assessed in animal studies. As in the regulation of outflow facility, cholinergic input stimulates the movement of the ciliary muscle to control the shape of the lens, and allows accommodation in conditions of low illumination. Accommodation is impaired in a vast majority of individuals and begins to become noticeable to the individual around the age of 40 years. Interestingly, changes in accommodative response occur much earlier in life, around 18 years of age, and progress until vision is noticeably impaired.

Physiological studies on accommodation are conducted following intraocular injection of a test compound and the results are compared relative to the results of control (untreated) animals. In the experiment, primates (for example, Rhesus monkeys) are treated twice a day for four days with 2 μg of prostaglandin $F_2\alpha$ ($PGF_2\alpha$). On days 5–8 both eyes are treated first with 2 μg of $PGF_2\alpha$-followed 2 hours later with an intraocular injection of 10 μL of the test compound at a final concentration of 1 mM. No injection is made to the control eye. 24 Hours after the last injection of the test compound, a course of therapy consisting of once a day dosing for a total of 4 days to measure accommodative responses to i.m. pilocarpine administration is performed following phenylephrine refraction.

Compounds of the invention can be tested to determine corneal penetration to the anterior chamber of the eye following topical administration of eye drops. For example, a test compound is assayed in vitro through an intact rabbit cornea for transcorneal penetration in a standard diffusion chamber apparatus. Corneas are mounted in a chamber at 37° C. with the epithelial side exposed to the test compound in Barany's solution. One mL samples are taken from the endothelial side 1 hour after addition of the test compound at a final concentration of 1 mM to the epithelial chamber. The volume of the chamber is replaced with phosphate buffered saline. The amount of test compound can be measured using any means that can be used to separate the compound and measure its concentration. For example, an HPLC with an attached UV detector can be used to determine the concentration of the test compound that has penetrated the cornea. Penetration values are also determined at later time points, for example, at 5 hours.

Assessment of corneal penetration of compounds of the invention can be determined in vivo, for example, in Cynomolgus monkeys. During these studies, the penetration of a test compound into the eye over a period of 5 hours is evaluated using an eyecup containing a solution of 10 mM of the test compound in Barany's solution. At the end of the experiment the eyecup is removed, the eye is repeatedly flooded with Barany's solution and a sample of intraocular fluid is removed from the anterior chamber with a needle inserted through the cornea. The quantity of the test compound in the intraocular fluid is determined using, for example, HPLC methods.

The activity of the compounds of the invention in breaking, reversing or inhibiting the formation of AGEs or AGE-mediated crosslinks can be assayed by any of the methods described in U.S. Pat. No. 5,853,703.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of decreasing intraocular pressure in an animal, including a human, comprising administering an intraocular pressure decreasing amount of a compound of the formula IA and or IB:

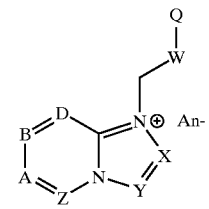

IA

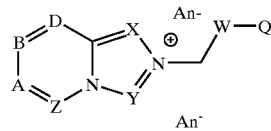

IB wherein:
  a. A and D are N and B and Z are respectively, $CR^B$ and $CR^Z$;
  b. $R^B$ and $R^Z$ are independently hydrogen, alkyl, alkoxy, allyl, alkylalkynyl, amino, acylamino, aroylamino, (aryl)(alkyl)amino, diarylamino, dialkcylamino, pyrrolidin-1-yl, piperidin-1-yl, 4-arylpiperidin-1-yl, 4-arylpiperazin-1-yl, 1-morpholin-4-yl, 1-thiamorpholin-4-yl, alkylthio, alkoxycarbonyl, carboxy, ($C_1$–$C_6$)-hydroxyalkyl, $H_2NS(O)_2$, $H_2NC(O)$, (alkyl)(alkyl)NC(O), 4-arylpiperazin-1-yl-C(O), fluoromethyl, difluoromethyl, trifluoromethyl, alkyl sulfonyl, alkylsulfinyl or arylsulfonyl;
  c. X and Y are independently N, N+(O—), or, respectively, $CR^X$ or $CR^Y$, with the proviso that there is only zero to one N-oxide;

d. $R^X$ and $R^Y$ are independently acetamido, hydrogen, alkyl, amino, —C≡$CR^E$, $CH_2$—C≡$CR^E$, alkylamino, dialkylamino, alkylthio, aryl, arylthio, arylalkyl, hydroxyalkyl, fluoromethyl, difluoromethyl, trifluoromethyl, cyanomethyl, alkoxycarbonylmethyl, 1-(alkoxycarbonyl)-1-hydroxyalkyl or aminocarbonylmethyl, wherein $R^E$ is alkyl, hydrogen or hydroxyalkyl;

e. W is C=O, CH(OH), $S(O)_2$ or S(O), or together with Q forms W—Q;

f. Q is Ar* or NR'R", or, W—Q together are Ar, cyano or —C≡$CR^Q$;

g. $R^Q$ is hydrogen, acylaminoalkyl, aroylaminoalkyl, alkyl, hydroxyalkyl, alkylaminoalkyl, dialkylaminoalkyl, (aryl)(alkyl)aminoalkyl, fluoromethyl, difluoromethyl, trifluoromethyl, Ar, ArCO, $ArS(O)_n$, where n=1 or 2, $H_2NC(O)$, or 4-arylpiperazin-1-yl-C(O);

h. R' and R" are independently hydrogen, alkyl, Ar, or together, NR'R" form a pyrrolidin-1-yl, piperidin-1-yl, 4-arylpiperidin-1-yl, 4-arylpiperazin-1-yl, 4-alkyl-piperazin-1-yl, 1-morpholin-4-yl or 1-thiamorpholin-4-yl ring;

i. Aryl is a $C_6$ to $C_{10}$ aromatic ring and Ar or Ar*, are each a $C_6$ or $C_{10}$ aromatic ring or a 5- or 6-membered heteroaromatic ring containing at least one and up to three atoms of N for the 6-membered heteroaryl ring and from one to three atoms of N or one atom of O or S and zero to two atoms of N for the 5-membered heteroaryl ring; each heteroaryl ring may be optionally substituted with up to two amino-, dialkylamino-, pyrrolidin-1-yl, piperidin-1-yl, 1-morpholin-4-yl, 1-thiamorpholin-4-yl, 4-arylpiperidin-1-yl, 4-arylpiperazin-1-yl-, or halo groups, or fused to a substituted benzene, pyridine, pyrimidine, pyridazine or triazine ring, and wherein $C_6$ or $C_{10}$ aromatic and heteroaromatic rings can be additionally substituted as set forth below;

j. An⁻ is a pharmaceutically acceptable anion;

k. $C_6$ or $C_{10}$ aromatic rings (including Ar, Ar*, or aryl), can be additionally substituted with acylamino, acyloxyalkyl, alkanoyl, alkanoylalkyl, alkenyl, alkoxy, alkoxycarbonyl, alkoxycarbonylalkyl, alkyl, —C≡$CR^E$, alkylamino, ($C_1$–$C_3$)-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, (C1–C6)-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl; and l. heteroaromatic rings (Ar or Ar*), can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, 1-morpholin-4-yl, 1-thiamorpholin-4-yl, 4-arylpiperazin-1-yl, sulfamoyl, aminosulfonyl ($H_2NSO_2$—), fluoromethyl, difluoromethyl or trifluoromethyl;

and pharmaceutically acceptable salts of said compounds.

2. The method of claim 1, wherein An⁻ is selected from the group consisting of chloride, bromide, mesylate, tosylate, brosylate, mesitylenesulfonate, acetate, maleate, fumarate and succinate.

3. The method of claim 1, wherein the compound is of the formula IA or IB, wherein Q is Ar* and:

c'. X and Y are independently N, or, respectively, $CR^X$ or $CR^Y$.

4. The method of claim 1, wherein the compound is of the formula IA or IB, wherein Q is NR'R" and:

c'. X and Y are independently N, or, respectively, $CR^X$ or $CR^Y$.

5. The method of claim 1, wherein the compound is of the formula IA or IB wherein W—Q is Ar and:

c'. X and Y are independently N, or, respectively, $CR^X$ or $CR^Y$.

6. A compound of the formula IA and or IB:

IA

IB wherein:

a. A and D are N and B and Z are respectively, $CR^B$ and $CR^Z$;

b. $R^B$ and $R^Z$ are independently hydrogen, alkyl, alkoxy, allyl, alkylalkynyl, amino, acylamino, aroylamino, (aryl)(alkyl)amino, diarylamino, dialkylamino, pyrrolidin-1-yl, piperidin-1-yl, 4-arylpiperidin-1-yl, 4-arylpiperazin-1-yl, 1-morpholin-4-yl, 1-thiamorpholin-4-yl, alkylthio, alkoxycarbonyl, carboxy, ($C_1$–$C_6$)-hydroxyalkyl, $H_2NS(O)_2$, $H_2NC(O)$, (alkyl)(alkyl)NC(O), 4-arylpiperazin-1-yl-C(O), fluoromethyl, difluoromethyl, trifluoromethyl, alkyl sulfonyl, alkylsulfinyl or arylsulfonyl;

c. X and Y are independently N, N+(O—), or, respectively, $CR^X$ or $CR^Y$, with the proviso that there is only zero to one N-oxide;

d. $R^X$ and $R^Y$ are independently acetamido, hydrogen, alkyl, amino, —C≡$CR^E$, —$CH_2$—C≡$CR^E$, alkylamino, dialkylamino, alkylthio, aryl, arylthio, arylalkyl, hydroxyalkyl, fluoromethyl, difluoromethyl, trifluoromethyl, cyanomethyl, alkoxycarbonylmethyl, 1-(alkoxycarbonyl)-1-hydroxyalkyl or aminocarbonylmethyl, wherein $R^E$ is alkyl, hydrogen or hydroxyalkyl;

e. W is C=O, CH(OH), $S(O)_2$ or S(O), or together with Q forms W—Q;

f. Q is Ar* or NR'R", or, W—Q together are Ar, cyano or —C≡$CR^Q$;

g. $R^Q$ is hydrogen, acylaminoalkyl, aroylaminoalkyl, alkyl, hydroxyalkyl, alkylaminoalkyl, dialkylaminoalkyl, (aryl)(alkyl)aminoalkyl, fluoromethyl, difluoromethyl, trifluoromethyl, Ar, ArCO, $ArS(O)_n$, where n=1 or 2, $H_2NC(O)$, or 4-arylpiperazin-1-yl-C(O);

h. R' and R" are independently hydrogen, alkyl, Ar, or together, NR'R" form a pyrrolidin-1-yl, piperidin-1-yl, 4-arylpiperidin-1-yl, 4-arylpiperazin-1-yl, 4-alkyl-piperazin-1-yl, 1-morpholin-4-yl or 1-thiamorpholin-4-yl ring;

i. Aryl is a $C_6$ to $C_{10}$ aromatic ring, and Ar or Ar*, are each a $C_6$ or $C_{10}$ aromatic ring or a 5- or 6-membered heteroaromatic ring containing at least one and up to three atoms of N for the 6-membered heteroaryl ring and from one to three atoms of N or one atom of O or S and zero to two atoms of N for the 5-membered heteroaryl ring; each heteroaryl ring may be optionally substituted with up to two amino-, dialkylamino-, pyrrolidin-1-yl, piperidin-1-yl, 1-morpholin-4-yl, 1-thiamorpholin-4-yl, 4-arylpiperidin-1-yl, 4-arylpiperazin-1-yl, or halo groups, or fused to a substituted benzene, pyridine, pyrimidine, pyridazine or triazine ring, and wherein $C_6$ or $C_{10}$ aromatic and heteroaromatic rings can be additionally substituted as set forth below;

j. $An^-$ is a pharmaceutically acceptable anion;

k. $C_6$ or $C_{10}$ aromatic rings (including Ar, Ar*, or aryl), can be additionally substituted with acylamino, acyloxyalkyl, alkanoyl, alkanoylalkyl, alkenyl, alkoxy, alkoxycarbonyl, alkoxycarbonylalkyl, alkyl, —C≡$CR^E$, alkylamino, $(C_1-C_3)$-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, (C1–C6)-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl; and l. heteroaromatic rings (Ar or Ar*), can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, 1-morpholin-4-yl, 1-thiamorpholin-4-yl, 4-arylpiperazin-1-yl, sulfamoyl, aminosulfonyl ($H_2NSO_2$—), fluoromethyl, difluoromethyl or trifluoromethyl;

and pharmaceutically acceptable salts of said compounds.

7. A pharmaceutical composition, comprising a compound of claim 6 and a pharmaceutically acceptable excipient.

* * * * *